United States Patent
Schuetz et al.

(10) Patent No.: US 9,333,147 B2
(45) Date of Patent: May 10, 2016

(54) DEVICE FOR SEALING A VESSEL AND METHOD OF MANUFACTURING A SEALED VESSEL

(75) Inventors: Andreas Schuetz, Stockdorf (DE); Makoto Kakiuchi, Ibaraki (JP); Seiji Shimazaki, Ibaraki (JP); Teruo Matsuda, Ibaraki (JP)

(73) Assignee: ARTE CORPORATION, Tokyo (JP)

( * ) Notice: Subject to any disclaimer, the term of this patent is extended or adjusted under 35 U.S.C. 154(b) by 536 days.

(21) Appl. No.: 13/814,915

(22) PCT Filed: Aug. 8, 2011

(86) PCT No.: PCT/EP2011/063582
§ 371 (c)(1),
(2), (4) Date: Apr. 9, 2013

(87) PCT Pub. No.: WO2012/019983
PCT Pub. Date: Feb. 16, 2012

(65) Prior Publication Data
US 2013/0197467 A1    Aug. 1, 2013

(30) Foreign Application Priority Data
Aug. 9, 2010   (JP) .................................. 2010-178974

(51) Int. Cl.
*A61J 1/20* (2006.01)
*A61M 5/28* (2006.01)
(Continued)

(52) U.S. Cl.
CPC ................ *A61J 1/2096* (2013.01); *A61J 1/065* (2013.01); *A61J 1/2093* (2013.01); *A61M 5/284* (2013.01);
(Continued)

(58) Field of Classification Search
CPC ....... A61J 1/065; A61J 1/2031; A61J 1/2093; A61J 1/2096; A61M 5/184; A61M 5/31511; A61M 2005/3123; B65B 3/003; B65B 2220/14; B65B 2230/02; B65B 63/00; B65B 63/08; B65B 7/28
See application file for complete search history.

(56) References Cited

U.S. PATENT DOCUMENTS 3,946,732 A * 3/1976 Hurscham ....................... 604/88
4,031,892 A    6/1977 Hurschman
(Continued)

FOREIGN PATENT DOCUMENTS

EP    0897708 A2    2/1999
EP    1816995 A2    8/2007
(Continued)

OTHER PUBLICATIONS

International Search Report and Written Opinion for PCT/EP2011/063582 mailed Nov. 18, 2011 (published as WO 2012/019983).

*Primary Examiner* — Philip R Wiest
*Assistant Examiner* — Benjamin Klein
(74) *Attorney, Agent, or Firm* — Choate, Hall & Stewart, LLP

(57) ABSTRACT

A device for sealing a vessel, in particular a cartridge (7) or a test-tube for accommodating a freeze-dried pharmaceutical product (S), wherein the vessel (1) comprises at its opening end (3) an opening edge (4) and an adjoining longitudinal portion (5) with an evenly formed inner cross section, including a front plunger (2) to be positioned inside the vessel (1) at the longitudinal portion (5), is characterized in that the front plunger (2) is configured to be positioned in the vessel (1) in a sealing state, in which the front plunger (2) is fully inserted in the vessel (1), or in an exchange state, in which the front plunger (2) is inserted partly in the vessel (1) and partly protrudes over the opening edge (4) of the vessel (1), wherein the front plunger (2) comprises sealing means that are configured to seal the inside of the vessel (1) against the outside when the front plunger (2) is positioned in the sealing state, and one or more communicating grooves (2i) that are configured to place the inside and outside of the vessel (1) in communication with each other when the front plunger (2) is positioned in the exchange state. Furthermore, a method of manufacturing a sealed vessel (1) is disclosed.

10 Claims, 16 Drawing Sheets

(51) Int. Cl.
  *A61J 1/06*  (2006.01)
  *B65B 7/28*  (2006.01)
  *B65B 63/00*  (2006.01)
  *B65B 63/08*  (2006.01)
  *B65B 3/00*  (2006.01)
  *A61M 5/315*  (2006.01)
  *A61M 5/31*  (2006.01)

(52) U.S. Cl.
  CPC . *B65B 3/003* (2013.01); *B65B 7/28* (2013.01);
    *B65B 63/00* (2013.01); *B65B 63/08* (2013.01);
    *A61J 1/2031* (2015.05); *A61M 5/31511*
    (2013.01); *A61M 2005/3123* (2013.01); *B65B*
    *2220/14* (2013.01); *B65B 2230/02* (2013.01)

(56) References Cited

U.S. PATENT DOCUMENTS

| | | | |
|---|---|---|---|
| 4,727,985 | A | 3/1988 | McNeirney et al. |
| 5,879,345 | A | 3/1999 | Aneas |
| 2004/0195276 | A1 | 10/2004 | Fuchs |
| 2005/0187303 | A1 | 8/2005 | Wu et al. |

FOREIGN PATENT DOCUMENTS

| | | |
|---|---|---|
| WO | WO-9413344 A1 | 6/1994 |
| WO | WO-2008/121298 A1 | 10/2008 |
| WO | WO-2009/061140 A2 | 5/2009 |
| WO | WO-2011/088471 A1 | 7/2011 |

\* cited by examiner

DEVICE FOR SEALING A VESSEL AND METHOD OF MANUFACTURING A SEALED VESSEL

BACKGROUND OF THE INVENTION

1. Field of the Invention

The present invention relates to a device for sealing a vessel, in particular a cartridge or a test-tube for accommodating a freeze-dried pharmaceutical product, wherein the vessel comprises at its opening end an opening edge and an adjoining longitudinal portion with an evenly formed inner cross section, including a front plunger to be positioned inside the vessel at the longitudinal portion.

Furthermore, the present invention relates to a method of manufacturing a sealed vessel, in particular a cartridge or a test-tube, containing a freeze-dried pharmaceutical product, wherein the vessel comprises at its opening end an opening edge and an adjoining longitudinal portion with an evenly formed inner cross section, at least comprising:

a drug solution provisioning step in which a drug solution to be freeze-dried is inserted into the vessel;

a drug solution sealing step in which the drug solution is sealed together with internal air by positioning a front plunger inside the vessel at the longitudinal portion; and a freeze-drying step in which the drug solution is freeze-dried so as to form the freeze-dried pharmaceutical product.

This application is a U.S. National Stage entry of International Application No. PCT/EP2011/063582, entitled "Device for Sealing a Vessel and Method of Manufacturing a Sealed Vessel", filed on Aug. 8, 2011, which claims the benefit of priority to Japanese Patent Application No. 2010-178974, filed Aug. 9, 2010, the contents of each of which are incorporated herein by reference in their entirety herein.

2. Description of Related Art

Many substances, in particular in the medical, pharmaceutical and chemical field like for instance pharmaceutical products or medically and/or biologically active substances, are sealed in vessels for storage purposes. Typically, they require careful sealing in order to preserve their stability and their specific characteristics over a given time period. Moreover, many of these substances are extremely expensive, and many of them also require careful handling when they are being administered. Examples for the substances in question include, for instance, injection drugs that have been newly developed in recent years for treating or preventing intractable diseases, in addition to cancer controlling drugs, cancer inhibiting drugs and the like.

As mentioned above, in many of these substances, the stability of their medicinal efficacy during storage is critical. Accordingly, in many cases a method is employed in which, in order for the pharmaceutical ingredient in the substance, e.g. a drug, to be preserved both safely and stably over a long period, a freeze-dried pharmaceutical product is prepared by freeze-drying the drug with the pharmaceutical ingredient so as to change it into powder form. When the freeze-dried pharmaceutical product is to be used, it is dissolved or suspended in a diluent or suspension (generically referred hereinafter simply as 'a diluent') so as to prepare an injection drug which is then administered to a patient.

Vessels employed in prior art for the above-mentioned purposes, once they are closed by means of a stopper or a plunger, are steadily sealed up to the moment when the vessel is opened for the purpose of using the sealed substance, e.g. in order to administer it to a human patient. As a consequence, during storage of the substance in the sealed vessel it is almost impossible to manipulate the sealed substance in any way, e.g. by releasing gas from the inside of the vessel, by freeze-drying the substance, by dissolving it in a diluent, by preparing it for administration to a patient, or the like. In order to carry out such manipulation the vessel has to be opened by completely releasing the stopper or plunger from the vessel. However, such procedure is not only extremely elaborate and time-consuming, but also comes along with various problems, for instance sterility problems or simply that the stopper or plunger gets lost during the substance manipulation procedure.

Hereinafter, the problems as outlined above are described in more detail with respect to the specific exemplary situation of industrially manufacturing dual chamber combined contained-cartridges and syringes including a freeze-dried pharmaceutical product. In prior art, in order to change an injection drug with a pharmaceutical ingredient into a freeze-dried pharmaceutical product, vials are filled with an injection drug in a liquid solution state, namely, with an injection drug solution, and freeze-drying processing is then performed on the individual vials in a low-temperature vacuum apparatus. As a result of this processing, the injection drug is changed into a freeze-dried pharmaceutical product, and the freeze-dried pharmaceutical product can be preserved by sealing the vials with rubber plungers and aluminum caps. When an injection drug is to be administered to a patient, a diluent that has been aseptically loaded into a separate container from that holding the freeze-dried pharmaceutical product is suctioned into an empty syringe. The injection needle of this syringe is then pushed through the rubber plunger of the vial and the diluent is injected into the vial. The freeze-dried pharmaceutical product is then dissolved or suspended inside the vial so as to create an injection drug. Preparations to enable the injection drug to be administered to a patient are completed by then suctioning this injection drug back into the syringe.

In this manner, because the task of suctioning a diluent from a container into a syringe, the task of injecting the diluent from this syringe into a vial in which a freeze-dried pharmaceutical product has been sealed, and the task of once again suctioning the injection drug prepared inside the vial back into the syringe must be performed in sequential stages, a considerable amount of labor and time are required. In addition, there is a possibility of the injection drug and injection equipment becoming contaminated with bacteria, foreign substances and the like while the injection drug is being transferred.

In order to solve such problems, dual chamber combined container-syringes have been developed (see, for example, Japanese Examined Patent Application, Second Publication No. H4-46152). In this dual chamber combined container-syringe, a front plunger is inserted into the distal end side of a cartridge, and a middle plunger is inserted into a central portion inside the cartridge so that the interior of the cartridge is divided into a front chamber and a rear chamber by the middle plunger. A bypass portion is formed in a portion of the cartridge on the distal end side of the middle plunger by expanding the diameter in the portion of the inner circumference of the cartridge. The front chamber, which is on the distal end side of the middle plunger, is filled with a freeze-dried pharmaceutical product which is then sealed therein, while the rear chamber, which is on the base end side of the middle plunger, is filled with diluent. The diluent inside the rear chamber is sealed therein by an end plunger that is inserted into the rearmost side of the cartridge interior.

When this dual chamber combined container-syringe is put to use, an injection needle is mounted onto a front assembly provided on the distal end side of the cartridge, and a plunger rod is inserted from the rear end side of the cartridge and is screwed into the end plunger so as to become fixed thereto. If the end plunger is pushed in using the plunger rod, the diluent which was sealed between the end plunger and the middle plunger moves forward together with these two plungers. When the middle plunger enters into the bypass portion of the cartridge, because the bypass portion has an expanded diameter, the sealing of the diluent by the middle plunger is released. As a result, the diluent passes through the bypass portion and enters into the front chamber which has been filled with the freeze-dried pharmaceutical product. The freeze-dried pharmaceutical product is dissolved by the diluent, and the injection drug to be administered to a patient is completed.

According to this dual chamber combined container-syringe, it is possible to perform the task of mixing together a freeze-dried pharmaceutical product and a diluent inside the cartridge by the simple action of pushing in the plunger rod. Accordingly, the operation is extremely convenient. Moreover, because the mixing action takes place inside the syringe, the injection drug does not come into contact with the outside air and any contamination of the injection drug by bacteria or foreign substances can be avoided.

The task of filling the interior of a cartridge with a freeze-dried pharmaceutical product in a dual chamber combined container-syringe is performed after, for example, the quantities of freeze-dried pharmaceutical products needing to be administered have been weighed. However, because the freeze-dried pharmaceutical product is in a powder form, the problem arises that, compared with liquids, precise quantities are difficult to measure. Because such freeze-dried pharmaceutical product is administered to human patients, it is necessary for accurate volumes thereof to be loaded into syringes.

A method in which freeze-drying processing is performed on each individual cartridge for liquid injection drugs (hereinafter, referred to as injection drug solutions) loaded into cartridges may also be considered. In this case, during the freeze-drying processing, it is necessary for the inside and outside of the cartridges to be in open communication with each other so that the injection drug solution is exposed to the atmosphere outside the cartridge. However, at times other than during freeze-drying processing, in order to secure the sterility of the cartridge interior, it has been necessary to place the interior of the cartridge in a sealed state and avoid the injection drug solution or freeze-dried pharmaceutical product coming into contact with the outside atmosphere.

Because several tens of hours are required to perform a single freeze-drying step, from the standpoint of work efficiency, it is preferable for freeze-drying to be performed simultaneously on a large quantity of cartridges.

In this case, because a certain length of time is needed until a predetermined number of cartridges containing injection drug solution are accumulated, it is not possible for the task of loading injection drug solution into a cartridge and the task of freeze-drying the injection drug solution to be performed without an intervening delay. Accordingly, it is necessary for cartridges loaded with an injection drug to have a sufficiently high level of sealability to allow them to be stored for a certain length of time. However, conventionally, no technology exists that, after a cartridge has been loaded with an injection drug and placed in a sealed state, enables the inside and outside of the cartridge to be in open communication with each other only during the freeze-drying processing. Accordingly, the problem has existed that it has not been possible to manufacture highly sterile dual chamber combined container-syringes at a superior level of productivity.

The present invention was devised in view of the above circumstances, and has an object to provide a device for sealing a vessel and a method of manufacturing a sealed vessel that ensures high levels of productivity and sterility of the sealed substances, and that enables the vessels to be filled with accurate quantities of freeze-dried pharmaceutical products.

SUMMARY OF THE INVENTION

In accordance with the present invention the aforementioned object is accomplished by a device for sealing a vessel comprising the features of claim 1. According to this claim such a device is characterized in that the front plunger is configured to be positioned in the vessel in a sealing state, in which the front plunger is fully inserted in the vessel, or in an exchange state, in which the front plunger is inserted partly in the vessel and partly protrudes over the opening edge of the vessel, wherein the front plunger comprises sealing means that are configured to seal the inside of the vessel against the outside when the front plunger is positioned in the sealing state, and one or more communicating grooves that are configured to place the inside and outside of the vessel in communication with each other when the front plunger is positioned in the exchange state.

Insofar, according to the invention it has been recognized that the problems initially outlined can be effectively avoided by employing a front plunger for sealing the vessel which is designed to be positioned either in a sealing state—in which the inside and the outside of the vessel are reliably sealed against each other by way of sealing means—or in an exchange state—in which the inside and the outside of the vessel are placed in communication with each other in a defined manner by way of communicating grooves. The front plunger according to the present invention is a kind of a self-opening front plunger that, when certain conditions are met, e.g. a pressure difference is provided between the inside and the outside of the vessel, moves from a sealing state quasi self-actingly towards the opening end of the vessel until it is positioned in the exchange state. By providing the communicating grooves it is assured that the conditions that cause the front plunger to move towards the opening end of the vessel, e.g. the pressure difference, are abolished as soon as the front plunger reaches the exchange states and, as a result, performs sort of "popping out" from the vessel. As a consequence, the movement of the front plunger is immediately stopped, and the front plunger is caused to remain in the exchange state, i.e. in a state in which it is still partly inserted in the vessel. This means that the front plunger is reliably saved from getting lost from the vessel.

For instance, in a specific application scenario, a vessel sealed with a device according to the present invention and containing a freeze-dried pharmaceutical product can be tightened with an infusion bag. By shifting the front plunger of the vessel into the exchange state it is then possible via the communicating grooves to mix the liquid from the infusion bag with the freeze-dried pharmaceutical product and to give the solved agent back into the infusion bag. Subsequently, the front plunger can be shifted back into the sealing state to reliably separate the content contained in the infusion bag from the content contained in the vessel.

According to a preferred embodiment the sealing means of the front plunger include at least one sealing rib, referred to as first sealing rib hereinafter, whose outer form is adapted to the form of the inner cross section of the longitudinal portion of the vessel. Typically, the outer form is a circular form, however, other forms are, in principle, also possible, among them for instance oval or quadratic forms.

In a specific embodiment the inner cross section of the longitudinal portion of the vessel has a circular form, and the first sealing rib has an outer diameter that is larger than the inner diameter of the longitudinal portion, and that is configured to elastically contract when the front plunger is positioned inside the vessel. As a consequence, when the front plunger has been inserted inside the vessel, the sealing rib forms a tight seal with the inner circumferential surface of the vessel. As a result, air-tightness and fluid-tightness can be secured inside the vessel.

Advantageously, the first sealing rib is dimensioned in such a way that the front plunger, when an underpressure of predefined strength is applied to the outer environment of the vessel, is caused to move inside the vessel towards its opening end. As a result of the movement of the front plunger caused by the pressure difference between the inside and the outside of the vessel, the front plunger is placed in the vessel in an exchange state, in which the inside and outside of the vessel are communicated with each other by means of the communicating grooves.

In the front plunger according to an aspect of the present invention, an inclined surface whose diameter gradually expands as it moves from the rear end side towards the front end side, and that extends in a circumferential direction of the sealing rib may be formed at a rear end portion of the first sealing rib. In this case, even if the inside and outside of the vessel are placed in communication with each other by means of the communicating groove, before the sealing rib has completely escaped from the vessel, the escape of the sealing rib from the vessel is accelerated by the elasticity of the sealing rib and by the inclined surface. Because the sealing rib sits at the opening end of the vessel as a result of escaping from the interior of the vessel in this manner, it is possible to improve the stability of the front plunger which is in the exchange state with respect to the vessel.

According to preferred embodiment the communicating grooves are formed in an outer circumferential surface of the front plunger extending from the inner end side of the front plunger up to the first sealing rib, in particular up to the center of the first sealing rib in the direction of a center axis of the front plunger. As a consequence, the duct between the inside and the outside of the vessel is established, while the first sealing rib still partly sits on the opening edge of the vessel. With respect to an easy manufacture of the front plunger, the communicating grooves are formed preferably with a substantially rectangular shape.

According to another preferred embodiment the sealing means include a positioning rib whose outer diameter is substantially the same as the inner diameter of the longitudinal portion of the vessel, and that is positioned further to the inner end side of the front plunger than the first sealing rib. Hence, when the front plunger is positioned in the exchange state and even if the first sealing rib completely escapes to the outside of the vessel, the positioning rib will still remain trapped inside the vessel. As a consequence the front plunger is prevented from accidentally coming out of the vessel.

Moreover, with respect to an equally distributed pressure release from the vessel, it proves to be beneficial that the communicating grooves are formed at intervals of equal or substantially equal distance along the circumferential direction of the front plunger.

In a specific embodiment of the present invention a front plunger is used in a dual chamber combined container-syringe (sometimes referred to herein as "DCPS" or "Lyo-DCPS"), which includes: a cartridge, in which the front plunger, a middle plunger, and an end plunger are positioned in this sequence from the opening end, a diluent, which is sealed inside the cartridge between the end plunger and the middle plunger, and a freeze-dried pharmaceutical product, which is sealed inside the cartridge between the middle plunger and the front plunger.

Furthermore, the aforementioned object is accomplished by a method of manufacturing a sealed vessel comprising the features of independent claim 10. According to this claim such a method is characterized in that the freeze-drying step includes:

surrounding atmosphere cooling processing in which a surrounding atmosphere which surrounds the vessel is cooled, such that the drug solution inside the vessel gets frozen;

pressure reduction processing in which, after the surrounding atmosphere has been cooled, the pressure of the surrounding atmosphere is reduced to below the pressure of the internal air, thereby causing the front plunger to move toward the opening end of the vessel and to rest in an exchange state, in which the front plunger is inserted partly in the vessel and partly protrudes over the opening edge of the vessel, such that one or more communicating grooves provided at the front plunger define a duct between the inside and the outside of the vessel through which solvent content can be removed by sublimation for enabling freeze-drying of the drug solution.

Insofar, according to the invention it has been recognized that a sealed vessel containing a freeze-dried pharmaceutical product can be efficiently and reliably manufactured by employing a front plunger that comprises communicating grooves as described in detail above. More specifically, according to the present invention a surrounding atmosphere cooling processing and a pressure reduction processing is applied by which the pressure of the surrounding atmosphere is reduced to below the pressure of the internal air contained in the vessel. In this way, a pressure difference is generated which acts on the front plunger causing it to move towards the opening end of the vessel. As a result, the front plunger is placed in the vessel in an exchange state. Consequently, because the inside and outside of the vessel are communicated with each other, it is possible to reliably perform freeze-drying on the drug solution inside the vessel using thermal conduction and radiation from the cooled surrounding atmosphere and by using pressure reduction as well. In the freeze-drying process the sublimate is released via the communicating grooves from the vessel to the surrounding environment. Moreover, since the front plunger is constructed in such a way that even in the exchange state it protrudes only partly over the opening edge of the vessel, but partly remains inside the vessel, the front plunger is prevented from accidentally coming out of the vessel. Accordingly, the freeze-dried drug solution can be easily and reliably sealed in a subsequent processing step.

According to a preferred embodiment the method constitutes a method of manufacturing a dual chamber combined container-syringe and comprises a diluent provisioning step and a diluent sealing step, both carried out before the drug solution provisioning step, in which a diluent is inserted into the vessel and sealed inside the vessel between the bottom of the vessel or an end plunger that has been inserted into the vessel and a middle plunger. When the freeze-dried drug solution is to be used it can be dissolved or suspended in the diluent, so as to prepare a drug which is then administered to a patient, for instance in form of an injection drug.

In a specific embodiment the diluent may be poured on top of the end plunger inside the vessel into which the end plunger has been inserted and may be sealed by inserting the middle plunger into the vessel so that air does not become contained in the diluent; and, thereafter, autoclave sterilization may be performed on the vessel. In this case, the diluent can be reliably sealed inside the cartridge, and the sterility of the solution can be secured.

In the method of manufacturing a dual chamber combined container-syringe according to an embodiment of the present invention, the freeze-drying step may be further provided with, between the pressure reduction processing and a sealing processing, substitution processing in which the surrounding atmosphere is substituted with an inert gas such as a nitrogen gas, such that the inside of the vessel is filled with the inert gas via the exposed communicating grooves. In this case, because moisture evaporated from the drug solution can be removed from the surrounding atmosphere, it is possible to prevent moisture remaining inside the vessel, and the quality of the freeze-dried pharmaceutical product can be maintained at a high level.

Moreover, after the freeze-drying has ended, by pushing the front plunger inside the vessel into a sealing state, in which the front plunger is fully inserted in the vessel, the freeze-dried pharmaceutical product obtained by freeze-drying the drug solution can be held in a sealed state. In addition, it may be provided that the front plunger is caused to move toward the rear end side of the vessel by applying to the outside of the vessel a pressure higher than the pressure of the inert gas contained in the vessel.

In the method of manufacturing a dual chamber combined container-syringe according to an embodiment of the present invention, the method may include, after the freeze-drying step, an assembly step in which a finger grip and a front assembly are mounted on the cartridge. By employing this structure, a completed dual chamber combined container-syringe can be obtained.

According to the method of manufacturing a dual chamber combined container-syringe and front plunger of the present invention, because it is possible for the inside and outside of the cartridge to be easily placed in communication with each other only when the injection drug solution is to be freeze-dried, it is possible to manufacture dual chamber combined container-syringes that have high levels of sterility and productivity, and that are able to be filled with accurate quantities of freeze-dried pharmaceutical products.

Furthermore, the present invention relates to a method of manufacturing a dual chamber combined container-syringe in which, in a cartridge in which a front stopper, a middle stopper, and an end stopper have been inserted in this sequence from the distal end side, a diluents is sealed between the end stopper and the middle stopper, and a freeze-dried pharmaceutical product is sealed between the middle stopper and the front stopper, comprising:

a diluent sealing step in which the diluents is sealed inside the cartridge by the end stopper and the middle stopper;

an injection drug solution sealing step in which an injection drug solution before freeze-drying is sealed together with internal air inside the cartridge by the middle stopper and the front stopper; and a freeze-drying step in which the injection drug solution is freeze-dried so as to form the freeze-dried pharmaceutical product, wherein the freeze-drying step includes:

surrounding atmosphere cooling processing in which a surrounding atmosphere which surrounds the cartridge is cooled;

pressure reduction processing in which, after the surrounding atmosphere has been cooled, by then reducing the pressure of the surrounding atmosphere to below the pressure of the internal air, the front stopper is placed in the cartridge in a half stoppering state; and sealing processing in which the front stopper in the half stoppering state is pushed inside the cartridge.

Still further, the present invention relates to a front stopper that is used in the above method of manufacturing a dual chamber combined container-syringe, comprising:

a sealing rib whose outer diameter is larger than the inner diameter of the cartridge, and that elastically contracts when the sealing rib is inserted inside the cartridge so as to form a tight seal with an inner circumferential surface of the cartridge;

a positioning rib that is positioned further to the rear end side than the sealing rib and whose outer diameter is substantially the same as the inner diameter of the cartridge; and a communicating groove that is formed in an outer circumferential surface of the front stopper, that extends from the positioning rib to the sealing rib, and that, when the front stopper is placed in the cartridge in the half stoppering state, places the inside and outside of the cartridge in communication with each other.

BRIEF DESCRIPTION OF THE DRAWINGS

FIG. 2A is a side view of the front plunger, while

DETAILED DESCRIPTION OF THE INVENTION

Hereinafter, embodiments of the present invention will be described in detail with reference made to the drawings.

Figure 1:
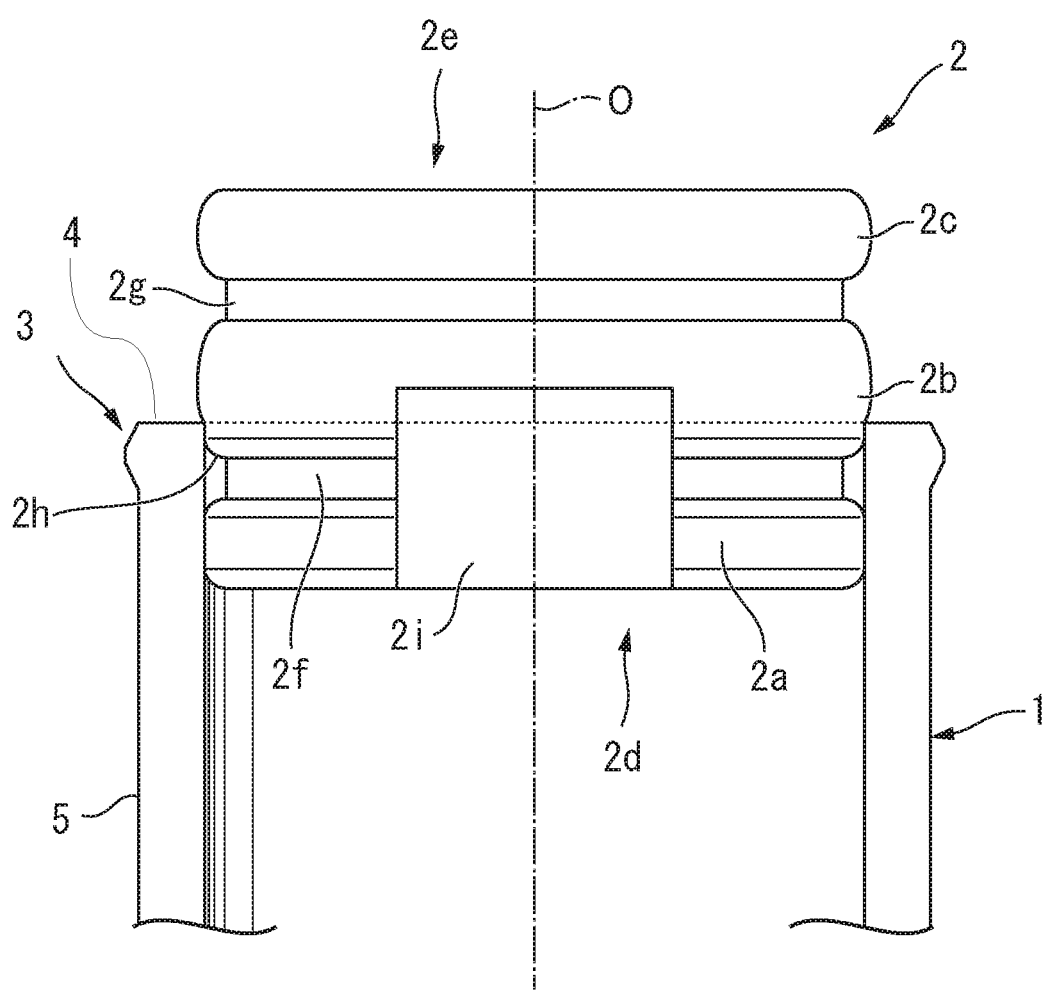
FIG. 1 is a side view illustrating a device for sealing a vessel including a front plunger according to an embodiment of the present invention.

With reference to FIG. 1, a device for sealing a vessel 1 including a front plunger 2 is illustrated, which is in accordance with the present invention. The vessel 1 comprises at its opening end 3 an opening edge 4 and an adjoining longitudinal portion 5 with an evenly formed inner cross section. In the illustrated embodiment, the longitudinal portion 5 is formed in a circular cylinder shape having the center axis O. Although a circular cylinder shape is the form that will be typically employed in most cases, it is to be understood that other shapes, e.g. rectangular, quadratic or oval ones, can also be employed in the same fashion, with the form of the front plunger 2 being specifically adapted.

Hereinafter, the structure of the front plunger 2 will be described in more detail.

As is shown in FIG. 1, the front plunger 2 has a form that is adapted to the form of the longitudinal portion 5 of the vessel 1, i.e. the front plunger 2 is formed in a substantially circular cylinder shape having the same center axis O as the vessel 1. Preferably, the front plunger 2 is formed from medical rubber such as butyl rubber that is able to resist chemical corrosion. However, it will be apparent to a skilled person that the invention is by no way limited to such material, and that depending on the specific characteristics of the substance to be sealed inside the vessel 1 other suitable materials can be employed likewise.

Figure 2A:
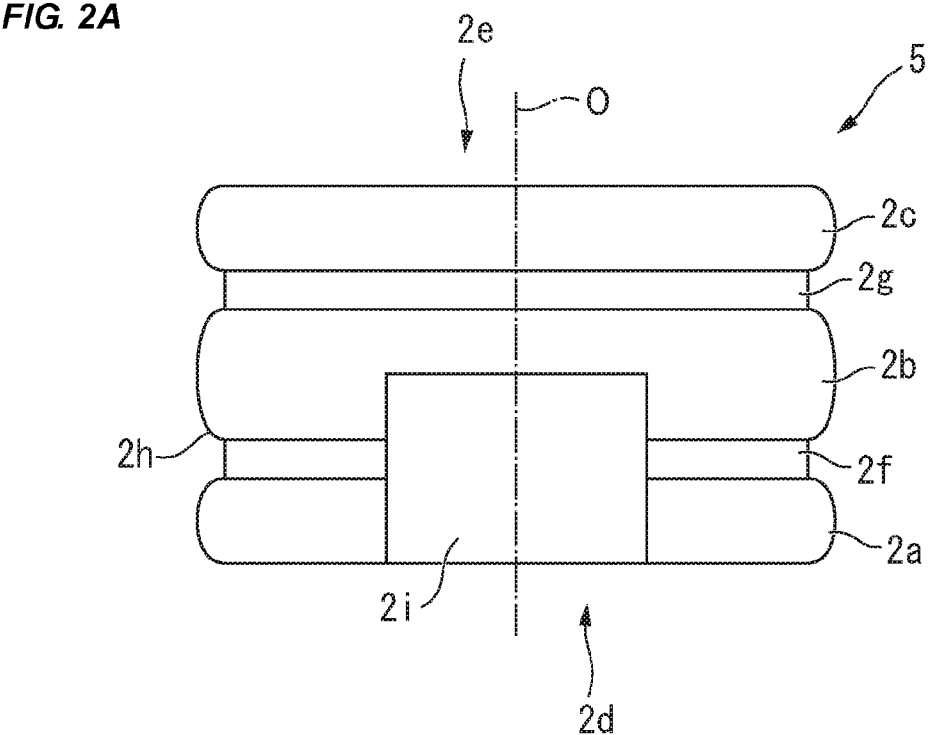
Figure 2B:
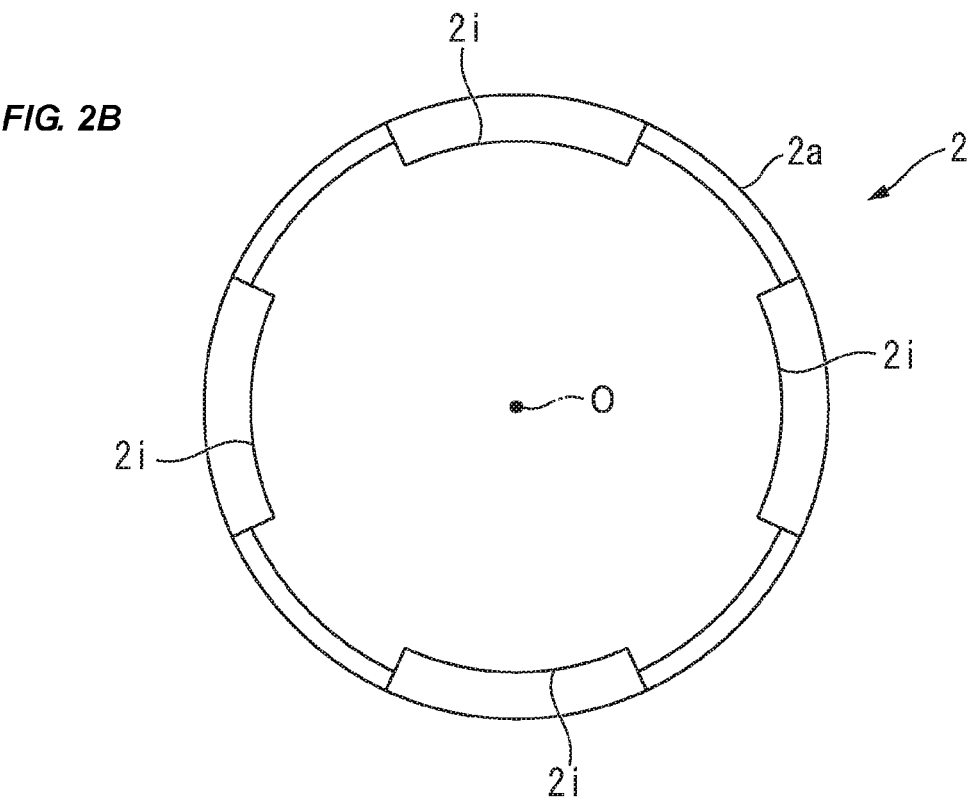
FIG. 2B is a view of the front plunger as seen from a rear end side thereof.

As is shown in FIGS. 2A and 2B, a positioning rib 2a, a first sealing rib 2b, and a second sealing rib 2c are formed on the outer circumferential surface of the front plunger 2 in this sequence moving from the inner end side 2d towards the outer end side 2e. The positioning rib 2a, first sealing rib 2b, and second sealing rib 2c are formed in ring shape by expanding the diameter of the outer circumferential surface of the front plunger 2, and each one extends around the entire surface in the circumferential direction thereof.

An outer diameter of the positioning rib 2a is set substantially identical to the inner diameter of the longitudinal portion 5 of the vessel 1. Each of outer diameters of the first sealing rib 2b and second sealing rib 2c is set larger than the inner diameter of the longitudinal portion 5 of the vessel 1. As a result of the diameters of the first sealing rib 2b and second sealing rib 2c elastically contracting, these ribs are able to be fitted inside the vessel 1. Air-tightness and fluid-tightness on the inner end side 2d of the front plunger 2 are secured by the first sealing rib 2b and second sealing rib 2c being placed in tight contact with the inner circumferential surface of the longitudinal portion 5 of the vessel 1.

A first valley portion 2f that has a narrower diameter than those of the positioning rib 2a and the first sealing rib 2b is formed between the positioning rib 2a and the first sealing rib 2b. In addition, a second valley portion 2g that has a narrower diameter than those of the first sealing rib 2b and the second sealing rib 2c is formed between the first sealing rib 2b and the second sealing rib 2c.

An outer edge of the first sealing rib 2b is shaped as a circular arc that, when viewed in a cross-section that includes the center axis O, protrudes outwards in the radial direction of the center axis O, and by this circular arc, an inclined surface 2h that gradually expands in diameter outwards in the radial direction of the center axis O as it moves from the inner end side 2d towards the outer end side 2e is formed on an inner end portion of the first sealing rib 2b. The inclined surface 2h extends around the entire circumference of the outer end portion of the first sealing rib 2b. It is noted that in the present embodiment, the inclined surface 2h is shaped as a circular arc when viewed in a cross-section that includes the center axis O, however, it is not limited to this and may also be formed as a straight line that slopes diagonally relative to the center axis O.

A plurality (four in the present embodiment) of communicating grooves 2i that extend from the inner end side 2d towards the outer end side 2e are formed at equal intervals in the circumferential direction in the outer circumferential surface of the front plunger 2. More specifically, the communicating grooves 2i are formed extending from the inner end side 2d of the front plunger 2, namely, from the positioning rib 2a up to the first sealing rib 2b. Namely, the communicating grooves 2i are open to the inner end and to the outer side in the radial direction of the front plunger 2.

It is noted that in the present embodiment, the communicating grooves 2i extend substantially to the center in the direction of the center axis O of the first sealing rib 2b, and also have a substantially rectangular shape when viewed from the side.

In the situation illustrated in FIG. 1, the front plunger 2 is positioned in the vessel 1 in an exchange state, in which the front plunger 2 is inserted partly in the vessel 1 and partly protrudes over the opening edge 4 of the vessel 1. This positioning of the front plunger 2 in the exchange state can be realized, for instance, by first positioning the front plunger 2 in the vessel 1 in a sealing state, in which the front plunger 2 is fully inserted in the vessel 1, and by then either applying a low pressure to the outside of the vessel 1 or generating a high pressure in the inside of the vessel 1. Under such conditions the front plunger 2 starts moving within the longitudinal portion 5 of the vessel 1 towards the opening end 3 thereof.

When the front plunger 2 reaches the opening end 3 of the vessel 1, first the second sealing rib 2c protrudes from the vessel 1 and, upon further movement, next the first sealing rib 2b protrudes from the vessel 1. In this position, the first sealing rib 2b expands in diameter, because the elastic contraction of the first sealing rib 2b has been released, and it sits on the opening edge 4 of the vessel 1.

Moreover, when the first sealing rib 2b starts protruding over the opening end 3 of the vessel 1, the communicating grooves 2i define a duct between the inside and the outside of the vessel 1, such that the inside of the vessel 1 is placed in contact with the outside of the vessel 1. In other words, the inside and outside of the vessel 1 communicate with each other via the communicating grooves 2i. As a result, the pressures inside and outside the vessel 1 arrive at a state of equilibrium, and the first sealing rib 2b quasi pops out of the vessel 1, thereby releasing the energy that was absorbed when pressing the front plunger 2 into the vessel 1.

In this regard it is important to recall that the outer diameter of the first sealing rib 2b is set (slightly) larger than the inner diameter of the longitudinal portion 5 of the vessel 1. Therefore, when the front plunger 2 is positioned with its first sealing rib 2b inside the vessel 1, the first sealing rib 2b is subject to an elastic pretension which, in turn, results in that the cross-sections of the openings of the communicating grooves 2i get increased. As a consequence, when the inside and the outside of the vessel 1 come into contact with each other via the communicating grooves 2i, the front plunger 2 is raised still a little further by means of the mechanical energy conserved in the front plunger 2 in form of the elastic compression of the first sealing rib 2b. Moreover, when the front plunger 2 has moved as far as the opening end 3 of the vessel 1 with the first and the second sealing, rib 2b, 2c completely protruding over the opening edge 4 of the vessel 1, the movement of the front plunger 2 is repressed, since the pressure which has been acting on the front plunger 2 is dissipated. However, in this situation the positioning rib 2a is still inserted inside the vessel 1. As a consequence, the front plunger 2 does not get entirely released from the vessel 1, but remains fitted on the vessel 1. Hence, the front plunger 2 can be easily pushed back into the vessel 1 and positioned in a sealing state, without requiring a new insertion of the inner end side 2d of the front plunger 2 into the vessel 1.

Figure 3:
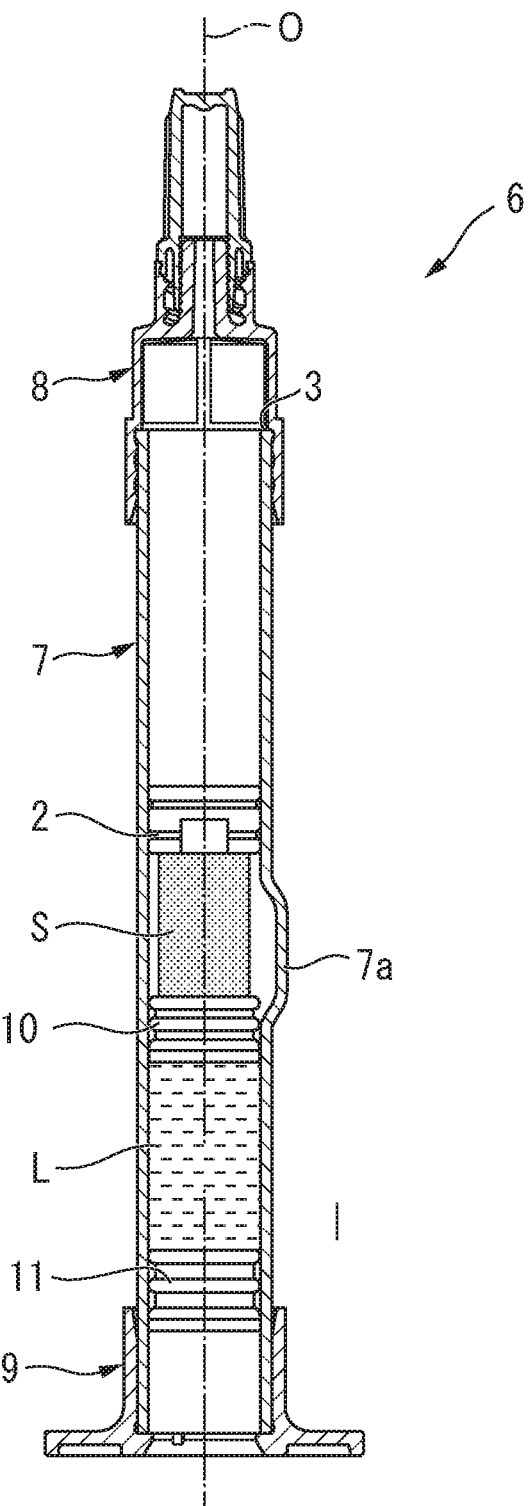
FIG. 3 is a schematic structural view showing a dual chamber combined container-syringe being equipped with a front plunger according to an embodiment of the present invention.

Turning now to FIG. 3, a description will be given of a method of manufacturing a sealed vessel according to an embodiment of the present invention. Specifically, the illustrated embodiment relates to manufacturing a dual chamber combined container-syringe (hereinafter, referred to simply as a combined container-syringe) 6. Same reference numerals refer to the same elements and components as employed in connection with the embodiment of FIGS. 1, 2A and 2B.

As is shown in FIG. 3, the combined container-syringe 6 is provided with a cartridge 7, a front assembly 8 that is mounted on a distal end portion (i.e., a top portion in FIG. 3) of the cartridge 7, a finger grip 9 that is made of synthetic resin and is fitted onto an outer circumference of a rear end portion of the cartridge 7, a front plunger 2, a middle plunger 10, and an end plunger 11. The front plunger 2, the middle plunger 10, and the end plunger 11 are fitted in this sequence inside the cartridge 7 from the distal end side.

A freeze-dried pharmaceutical product S is sealed between the front plunger 2 and the middle plunger 10, and a diluent L is sealed between the middle plunger 10 and the end plunger 11. A bypass portion 7a that is formed by expanding the diameter of a portion of the inner circumferential surface of the cartridge 7 is provided in the cartridge 7 at a position further to the distal end side than the location where the middle plunger 10 is placed.

The freeze-dried pharmaceutical product S is manufactured in powder form by performing freeze-drying processing on an injection drug solution (i.e., a pharmaceutical ingredient) M. The diluent L is used to restore the injection drug solution by dissolving or suspending the freeze-dried solution S therein.

In this combined container-syringe 6, if the end plunger 11 is pushed in towards the distal end side using a plunger rod (not shown), the diluent L that is sealed between the end plunger 11 and the middle plunger 10 moves forwards together with the end plunger 11 and the middle plunger 10. When the middle plunger 10 reaches the bypass portion 7a of the cartridge 7, because the bypass portion 7a has an expanded diameter, the sealing of the diluent L by the middle plunger 10 is released. As a result, the diluent L passes through the bypass portion 7a and flows into the side which has been filled with the freeze-dried pharmaceutical product S. An injection drug to be administered to a patient is completed when the freeze-dried pharmaceutical product S is dissolved by the diluent L. Using the above procedure, the injection drug is changed into a state in which it can be administered to a patient.

Figure 4:
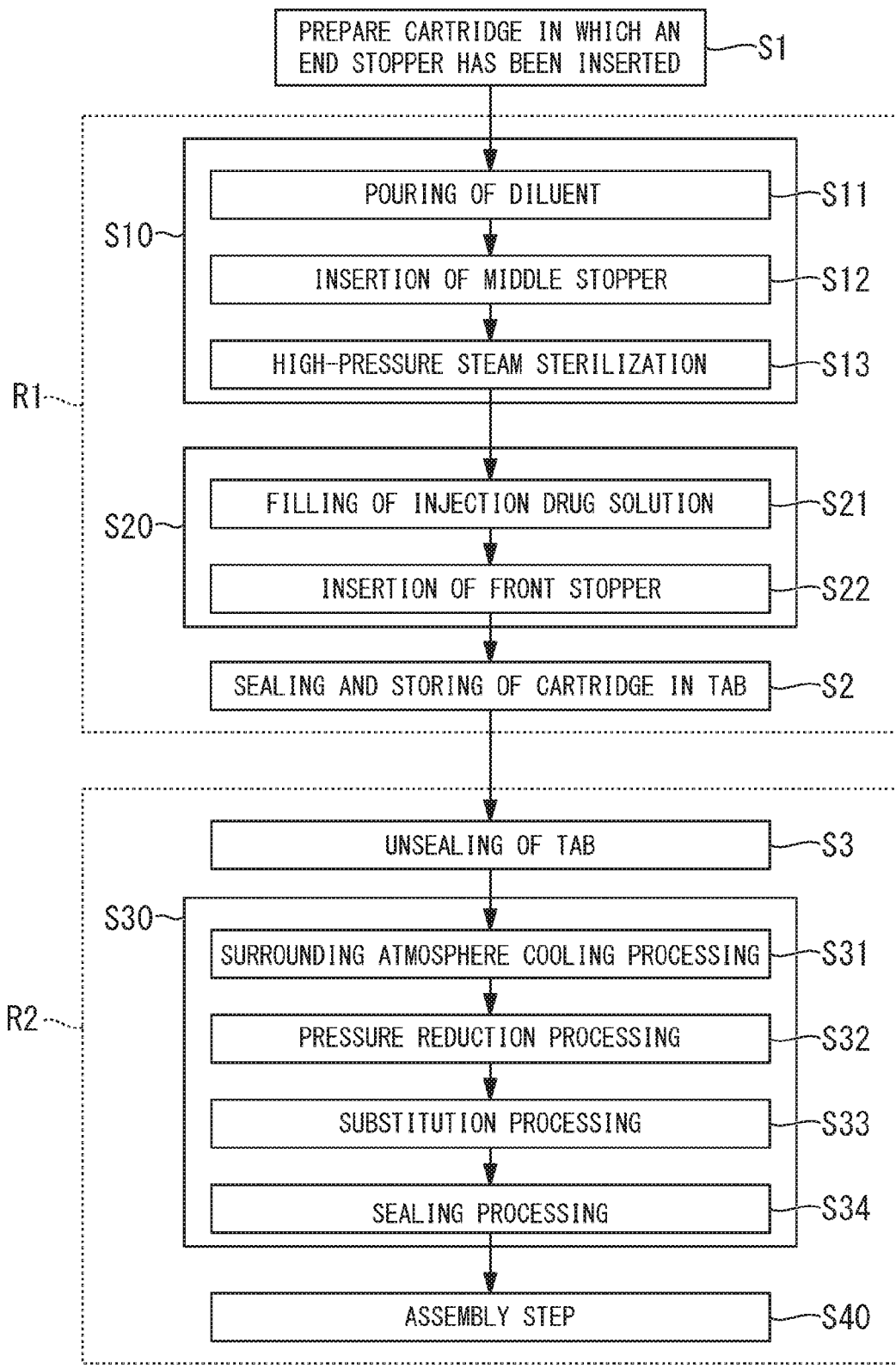
FIG. 4 is a flowchart showing a method of manufacturing the dual chamber combined container-syringe according to the embodiment.

Next, a method of manufacturing the combined container-syringe 6 having the above described structure will be described with reference made to the flowchart shown in FIG. 4. This manufacturing method principally comprises a diluent sealing step S10, an injection drug solution sealing step S20, a freeze-drying step S30, and an assembly step S40.

Figure 5A:
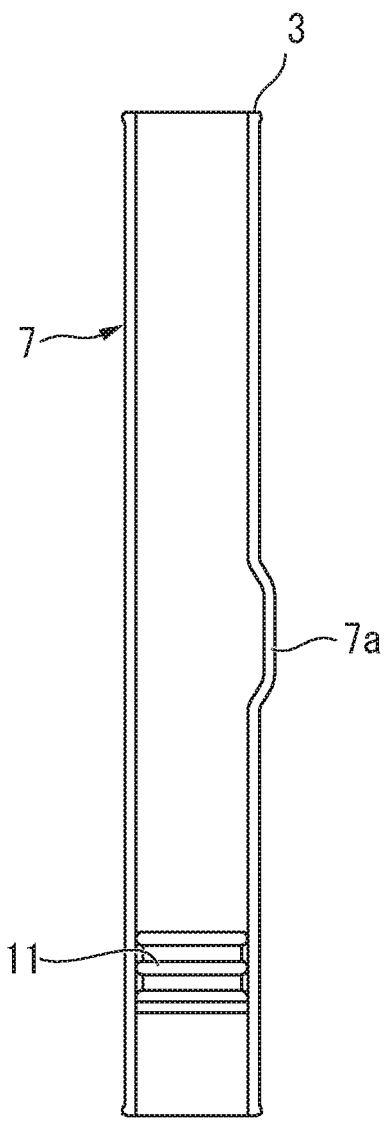
FIGS. 5A and 5B are views illustrating a solution sealing step.

Firstly, as is shown in FIG. 5A, the cartridge 7 into whose rear end side the end plunger 11 has been inserted is prepared (S1). The diluent sealing step S10 is performed on this cartridge 7 that is provided with the end plunger 11. It is noted that the diluent sealing step S10 is conducted inside a clean room R1.

In the diluent sealing step S10, firstly, when the cartridge 7 has been positioned such that the distal end side thereof faces upwards, diluent L is poured inside the cartridge 7 (S11). At this time, because the rear end side of the interior of the cartridge 7 is closed off by the end plunger 11, the diluent L is poured on top of the end plunger 11 inside the cartridge 7.

Figure 5B:
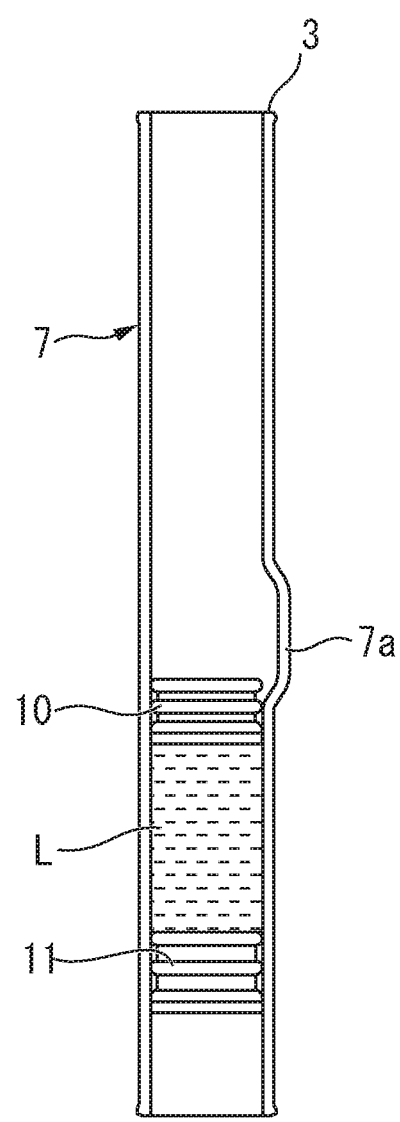

Then, the middle plunger 10 is inserted from the distal end side of the cartridge 7 (S12) so that the diluent L is sealed between the middle plunger 10 and the end plunger 11. This task is conducted while the air inside the cartridge 7 into which the middle plunger 10 has been inserted is being suctioned out, namely, while the interior of the cartridge 7 is being placed in a vacuum state. As a result, it is possible to prevent air penetrating between the middle plunger 10 and the end plunger 11 and, as is shown in FIG. 5B, nothing other than the diluent L is sealed between the middle plunger 10 and the end plunger 11. Namely, by bubble free filling of the diluent L in this manner, it is possible to prevent air bubbles becoming mixed into the diluent L in this space.

Then, autoclave sterilization is performed on the cartridge 7 inside which the diluent L has been sealed in this manner (S13). As a result, the diluent sealing step S10 is completed.

Next, the injection drug solution sealing step S20 is performed on the cartridge 7 inside which the diluent L has been sealed in the manner described above. The injection drug solution sealing step S20 is also conducted inside the clean room R1 in the same way as the diluent sealing step S10.

Figure 6A:
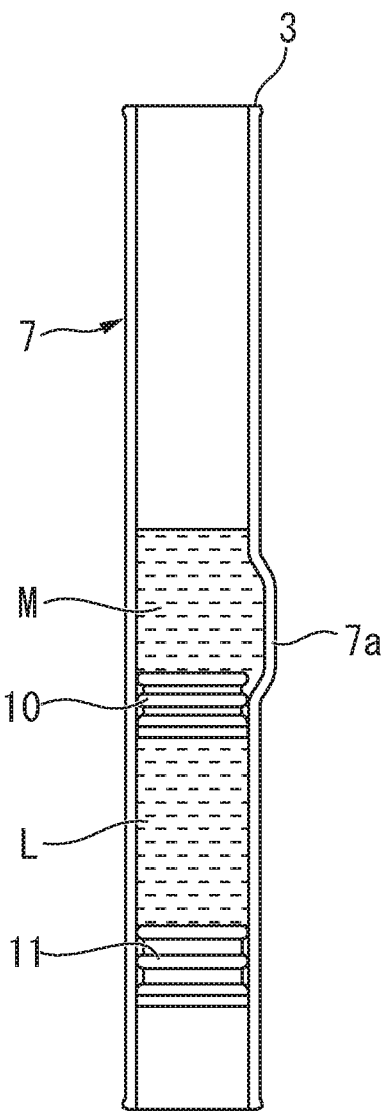
FIGS. 6A and 6B are views illustrating an injection drug solution sealing step.

In the injection drug solution sealing step S20, when the cartridge 7 has been positioned such that the distal end side thereof faces upwards, injection drug solution M (i.e., active pharmaceutical ingredient solution) is poured inside the cartridge 7 (S21). At this time, because the interior of the cartridge 7 is closed off by the middle plunger 10 at a point substantially in the center in the direction of the center axis O, as is shown in FIG. 6A, the injection drug solution M is poured on top of the middle plunger 10 inside the cartridge 7.

Figure 6B:
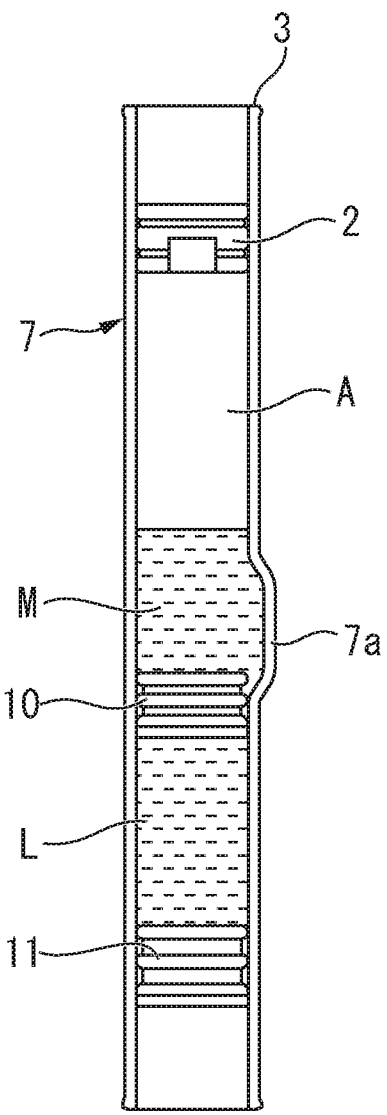

Then, as is shown in FIG. 6B, the front plunger 2 is inserted from the distal end side of the cartridge 7 (S22) so that the injection drug solution M is sealed between the front plunger 2 and the middle plunger 10. At this time, gas inside the clean room R1 is also sealed between the front plunger 2 and middle plunger 10 of the cartridge 7 together with the injection drug solution M. Namely, between the front plunger 2 and middle plunger 10 of the cartridge 7 are sealed both the injection drug solution M and internal air A. As a result, the injection drug solution sealing step S20 is completed.

Next, the cartridge 7 which has completed the diluent sealing step S10 and the injection drug solution sealing step S20 is stored in a tub (not shown) inside the clean room R1 (S2). A nest that is capable of holding a plurality of the cartridges 7 is provided inside the tub, and the cartridges 7 which have completed the diluent sealing step S10 and the injection drug solution sealing step S20 are stored sequentially within the tub. At a point when a predetermined number of cartridges 7 have been accumulated, the tub is sealed shut, namely, the cartridges 7 are sealed and stored in the tub (S2).

The tub in which the cartridges 7 are stored is transported to a freeze-drying chamber R2, and the sealed tub is opened inside the freeze-drying chamber R2 (S3). In this manner, the sterility of the cartridges 7 is maintained by sealing and storing them inside the tub during transporting.

Next, the freeze-drying step S30 is performed inside the freeze-drying chamber R2. The freeze-drying step S30 is conducted with the cartridges 7 being oriented such that the distal end sides thereof are facing upwards.

In the freeze-drying step S30, cooling processing S31 is performed in order to lower the temperature inside the freeze-drying chamber R2, namely, in order to cool the surrounding atmosphere and the shelves where the cartridges 7 have been placed. It is noted that in the cooling processing S31, it is preferable for the temperature of the surrounding atmosphere and the temperature of the shelves where the cartridges 7 have been placed to be cooled to −40° C. or less and more preferably to −50° C. By doing this, the diluent L and the injection drug solution M inside the cartridge 7 are frozen.

After the surrounding atmosphere and the shelves where the cartridges 7 have been placed have been sufficiently cooled, pressure reduction processing S32 is performed in order to reduce the pressure of the surrounding atmosphere by decompressing the interior of the freeze-drying chamber R2. At this time, the value of the pressure of the surrounding atmosphere is sufficiently reduced below the pressure of the internal air A located between the middle plunger 10 and front plunger 2 inside the cartridge 7.

Figure 7:
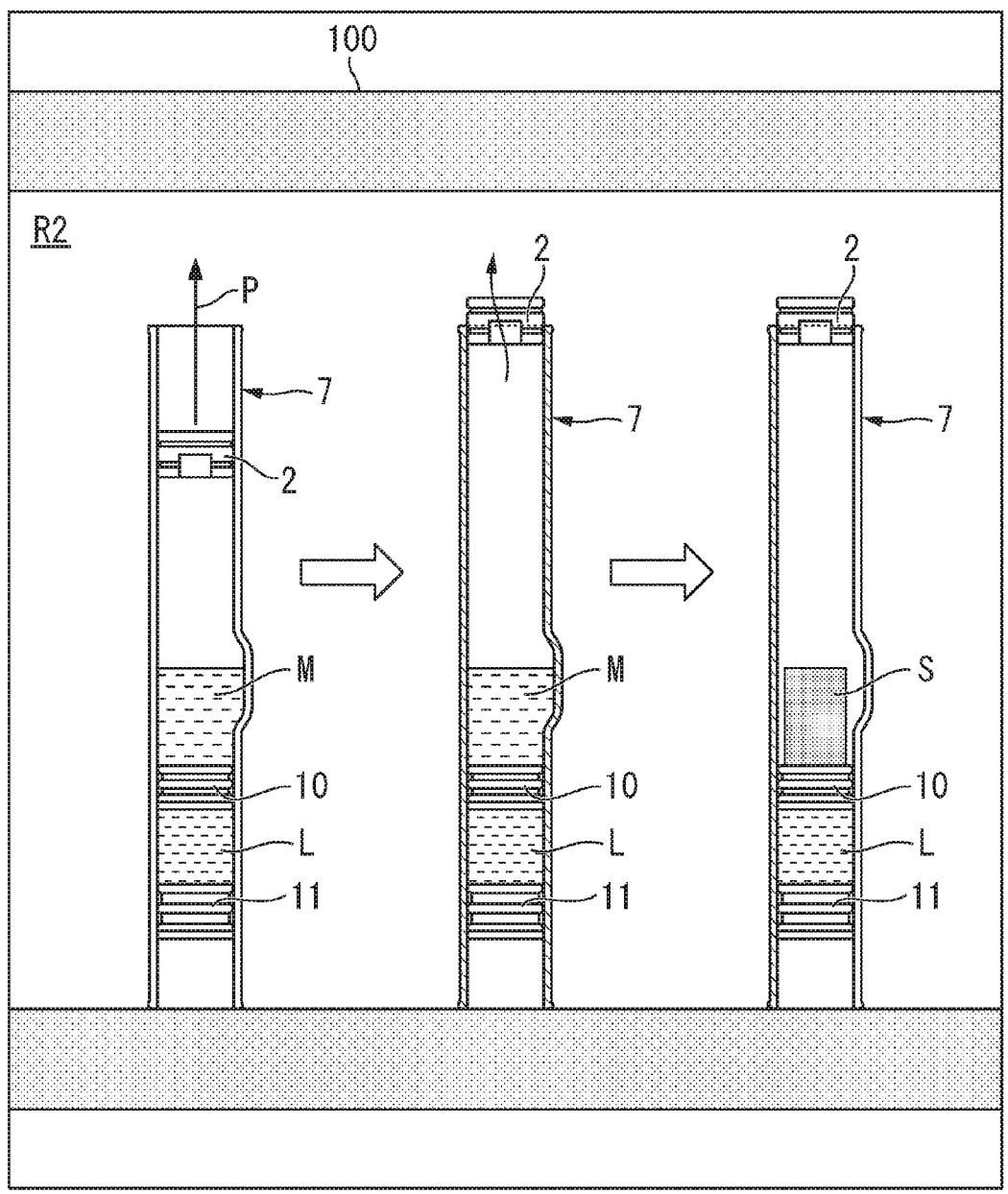
FIG. 7 is a view illustrating a freeze-drying step.

As a result of this, as is shown on the left side in FIG. 7, due to the pressure difference between the internal air A and the surrounding atmosphere, pressure P acts on the front plunger 2 inserted inside the cartridge 7 in the direction of the distal end side of the cartridge 7 (i.e., in an upward direction).

As a result of the pressure P acting on the front plunger 2 in this manner, the front plunger 2 moves upwards, namely, towards the distal end side of the cartridge 7. When the front plunger 2 reaches the distal end of the cartridge 7—this situation corresponds to the state that is illustrated in more detail in FIG. 1—the first sealing rib 2b and the second sealing rib 2c protrude from the cartridge 7. In addition, the communicating grooves 2i are exposed to the outside of the cartridge 7 so that the inside and outside of the cartridge 7 communicate with each other via the communicating grooves 2i. Namely, because the front plunger 2 is positioned in an exchange state (which can be considered as a half plungering state) by being pushed only halfway into the cartridge 7, the pressures inside and outside the cartridge 7 becomes in a state of equilibrium. As a result of this, because the pressure P which has been acting on the front plunger 2 is dissipated, the movement of the front plunger 2 is stopped by the positioning rib 2a and the front plunger 2 stops at the distal end of the cartridge 7, as illustrated in the center in FIG. 7. In this exchange state the front plunger 2, depending on its specific construction, may have been lifted such that the protrusion over the opening end 3 of the cartridge 7 is in the range of approximately 1 mm.

Best freeze-drying results are obtained when the communicating grooves 2i are formed to extend from the inner end side 2e of the front plunger 2 up to the middle of the first sealing rib 2b, i.e. up to the position of the first sealing rib 2b that has the largest diameter, as shown in FIG. 2A. Due the elastic compression of the first sealing rib 2b when being positioned inside the cartridge 7, the cross-sections of the openings of the communicating grooves 2i get enlarged. As a result, when the inside and outside of the cartridge 7 start getting into communicating contact with each other, the mechanical energy stored in the front plunger 2 due to its compression gets released and causes the front plunger 2 to get lifted still further. Thereby, a returning of the front plunger 2 from the exchange state back to the sealing state is effectively avoided, and the resulting duct formed by the communicating grooves 2i is sufficiently large to enable freeze-drying of the injection drug solution M in a reliable fashion.

Moreover, when the front plunger 2 has moved as far as the distal end of the cartridge 7, the positioning rib 2a is still inserted inside the cartridge 7, while the first sealing rib 2b expands in diameter, because the elastic contraction of the first sealing rib 2b has been released, and sits on the distal end 7b of the cartridge 7.

As is further shown in the center in FIG. 7, the water content of the injection drug solution M is expelled to the outside via the communicating grooves 2i by sublimation. If this state is preserved for a short time, then as is shown on the right side in FIG. 7, the injection drug solution M changes to the freeze-dried pharmaceutical product S.

Thereafter, substitution processing S33 is performed in order to substitute the air inside the freeze-drying chamber R2 with pure nitrogen of a previously set level (at, for example, approximately 800 mbar). By doing this, any moisture inside the freeze-drying chamber R2 is eliminated, and the interior of the cartridge 7 is filled with a predetermined amount of pure nitrogen via the communicating grooves 2i.

Figure 8:
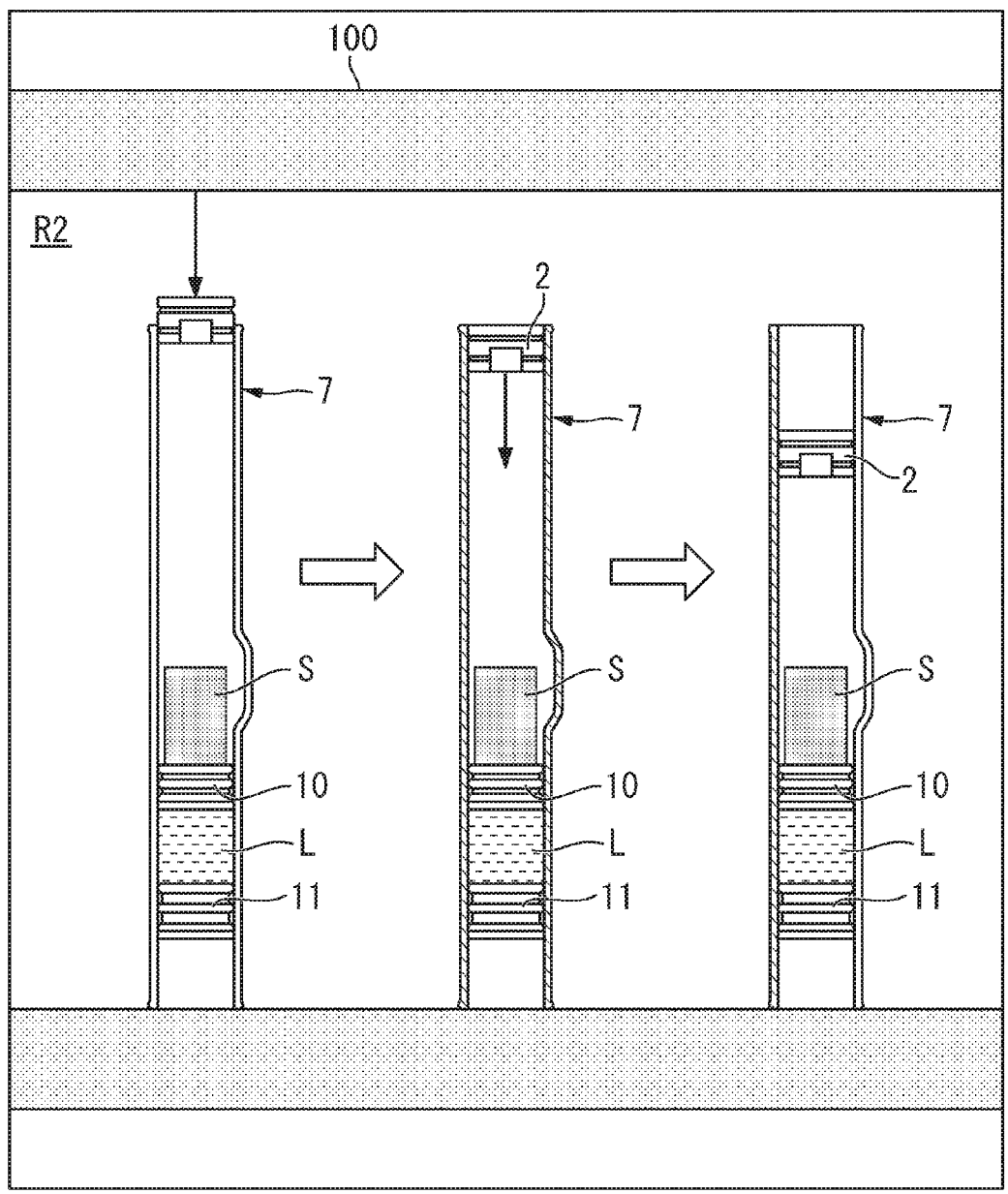
FIG. 8 is a view illustrating a sealing processing step after the freeze-drying.
Figure 9A:
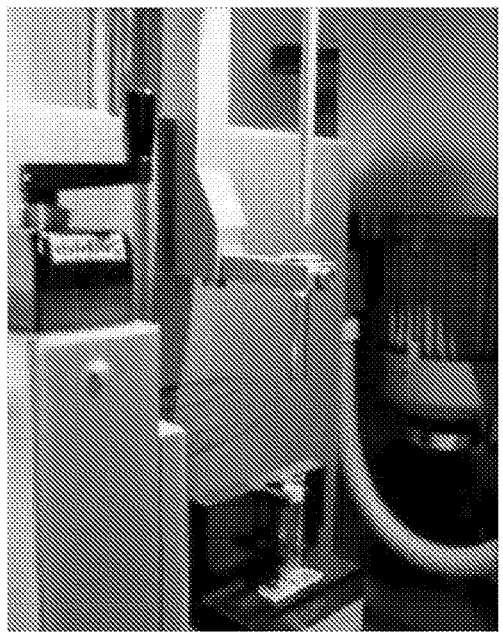
FIG. 9A shows the positioning of the end stopper (plunger)
Figure 9B:
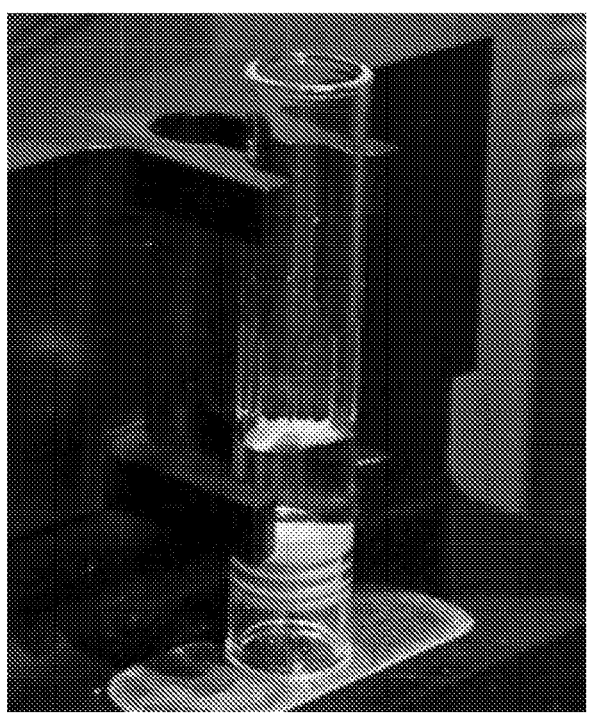
FIG. 9B shows the filling of the diluent
Figure 9C:
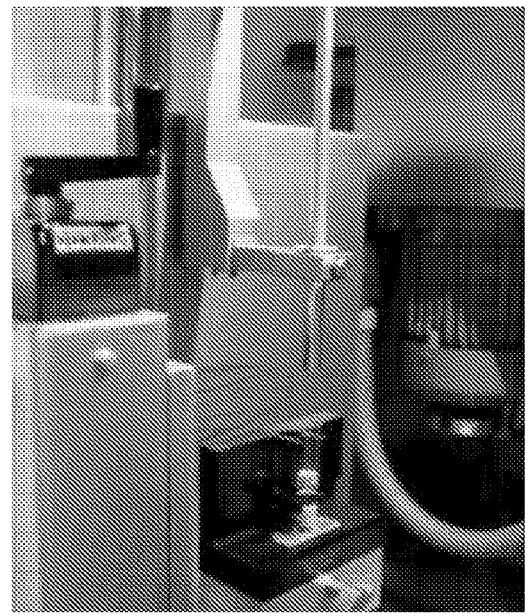
FIG. 9C shows the positioning of the middle stopper (plunger)
Figure 9D:
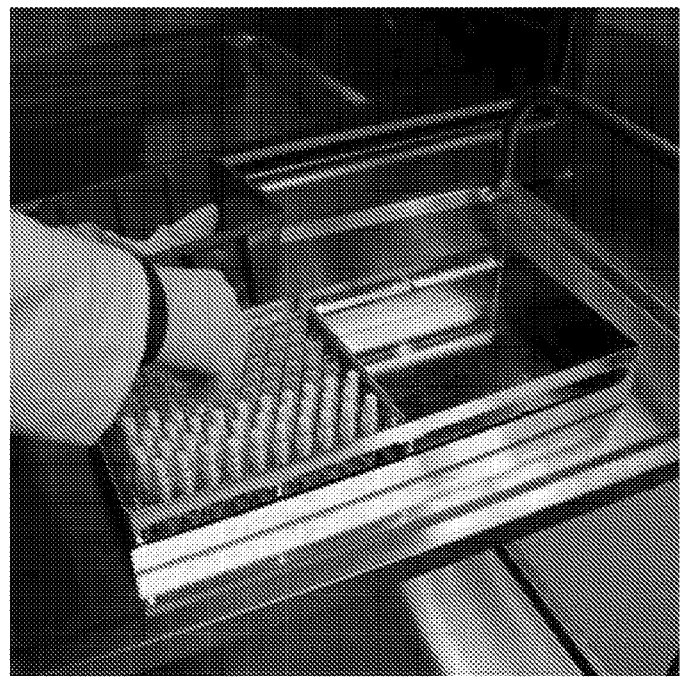
FIG. 9D shows the placing of distance rods
Figure 9E:
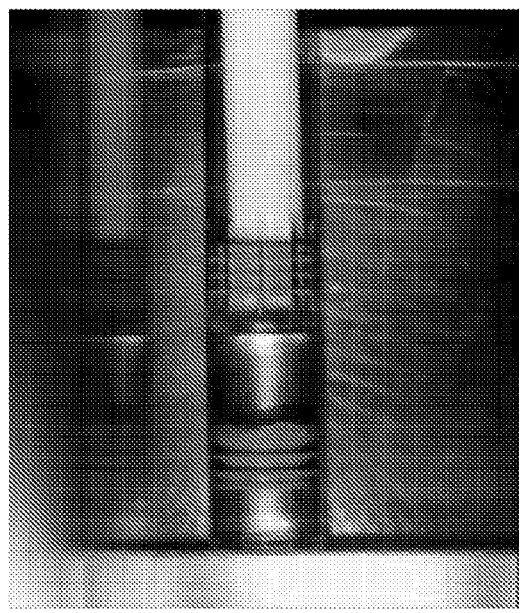
FIG. 9E shows the drawing of vacuum in the lyophilizer (lyo)
Figure 9F:
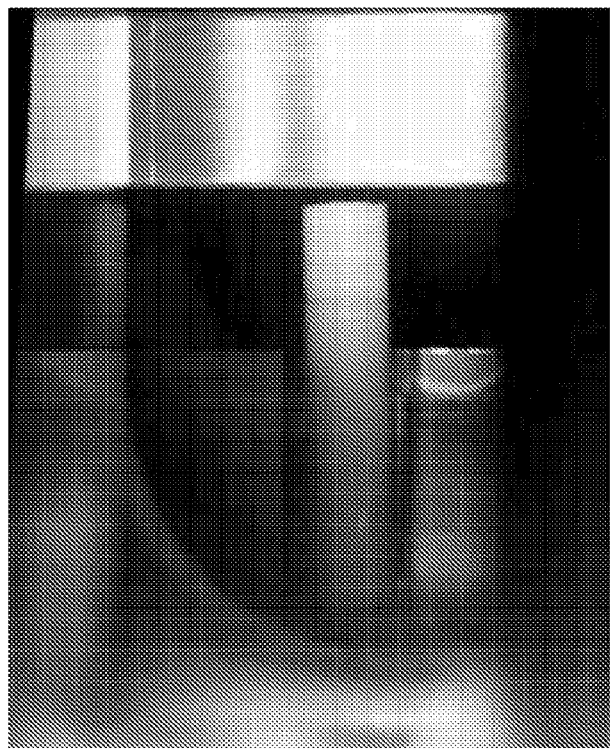
FIG. 9F shows the pushing down of rods
Figure 9G:
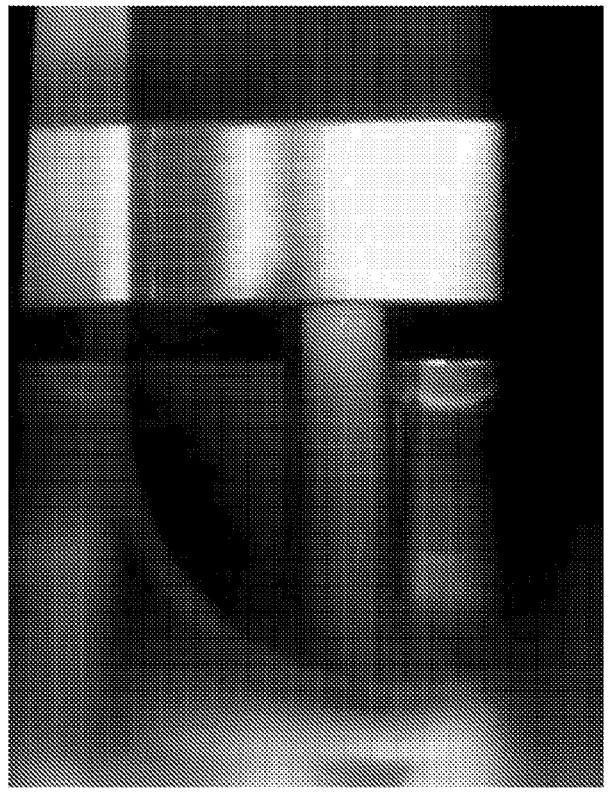
FIG. 9G shows the pushing down of rods (end position)
Figure 9H:
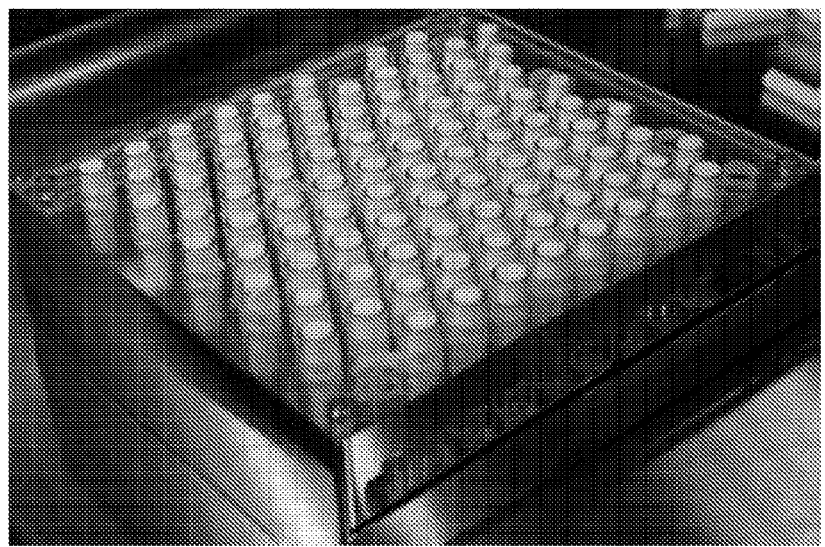
FIG. 9H shows the unloading of lyophilizer (lyo)
Figure 9:
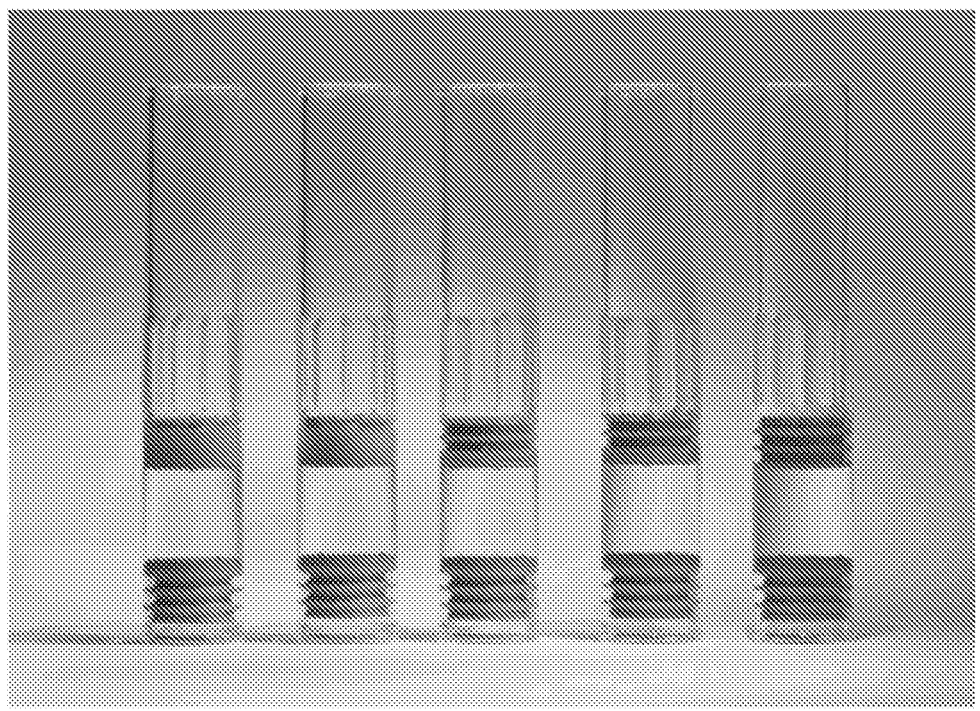
FIG. 9I shows bubble free filled carpules
Figure 10A:
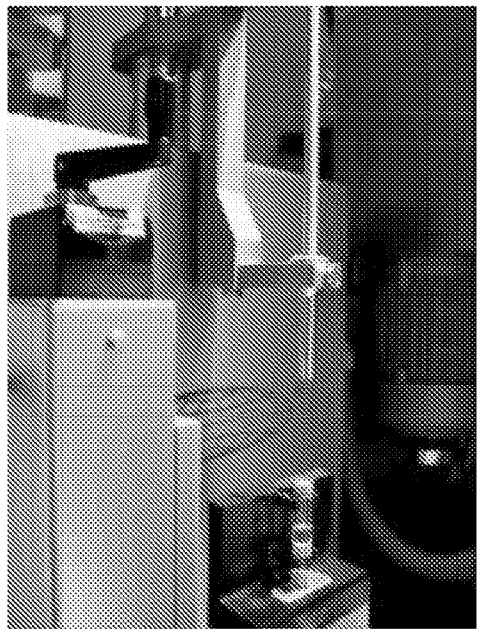
FIG. 10A shows the filling of the lyophilisation solution and positioning of the lyo stopper (plunger)
Figure 10B:
FIG. 10B shows the loading of the lyophilizer
Figure 10C:
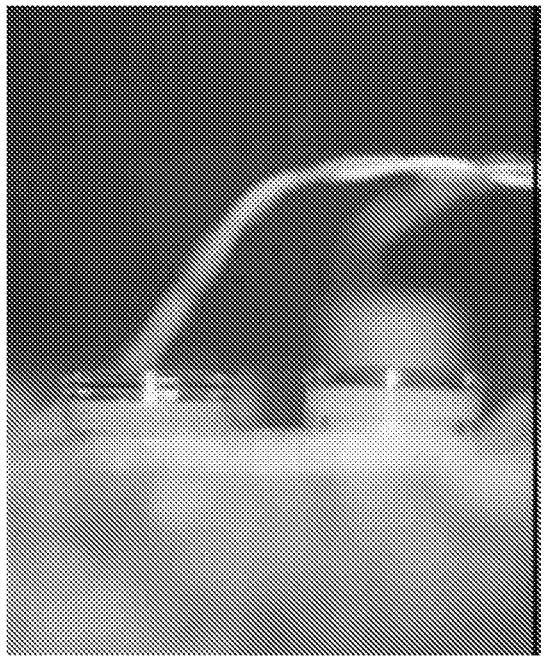
FIG. 10C shows the self-opening of the lyo stoppers in the lyophilizer
Figure 10D:
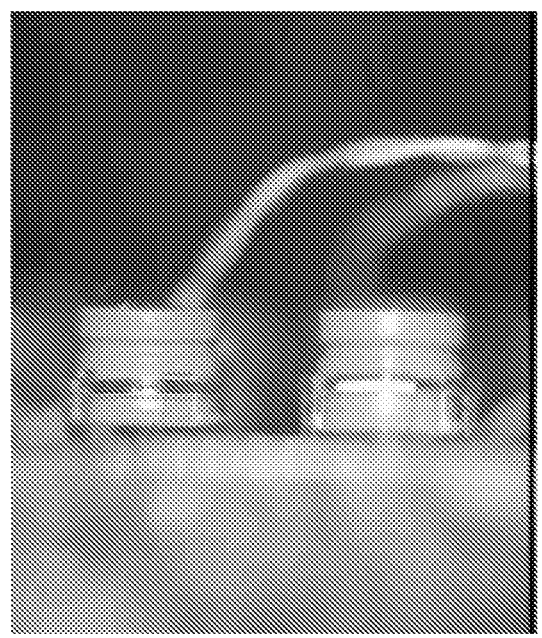
FIG. 10D shows lyo stoppers in lyo position

Next, sealing processing S34 is performed. Here, as is shown on the left side in FIG. 8, a shelving plate 100 which has been placed above the cartridges 2 inside the freeze-drying chamber R2 is moved downwards while the horizontal state thereof is maintained. As a result of this, the shelving plate 100 presses against the front plungers 2 of each of the plurality of cartridges 7 and, as is shown in the center in FIG. 8, the front plungers 2 are pushed into the cartridges 7.

The front plungers 2 which have been pushed inside the cartridges 7 in this manner move downwards due to the pressure difference between the inside and the outside of the cartridges 7. Ultimately, as is shown on the right side in FIG. 8, the front plungers 2 are positioned in an appropriate location as their placement position.

Thereafter, in the assembly step S40, the front assembly 8 is fitted onto the distal end portion of each cartridge 7, and the finger grip 9 is fitted on to the rear end portion of each cartridge 7. As a result, the combined container-syringe 6 such as that shown in FIG. 3 is completed.

According to the above described method of manufacturing the combined container-syringe 6, in the freeze-drying step S30, after the surrounding atmosphere and the shelf on which have been placed the cartridges 7 having the injection drug solution M sealed inside them have been cooled, by reducing the pressure of the surrounding atmosphere to less than that of the internal air A between the middle plunger 10 and the front plunger 2 inside the cartridge 7, a pressure difference is generated between the surrounding atmosphere and the internal air A. When this pressure difference then acts on the front plunger 2, the front plunger 2 moves towards the distal end side of the cartridge 7 and, as a result, the front plunger 2 is in the exchange state by being pushed halfway into the cartridge 7. Consequently, the inside and outside of the cartridges 7 are in communication with each other, and because the pressure is further reduced, the injection drug solution M can be freeze-dried.

Here, because, for example, several tens of hours are required for the freeze-drying step S30, from the standpoint of work efficiency, it is preferable for a large quantity of cartridges 7 to be freeze-dried at the same time. In this case, because a certain length of time is required until a predetermined number of cartridges 7 containing the injection drug solution M are accumulated, it is not possible to perform the task of pouring the injection drug solution M into the cartridges 7 and the freeze-drying of the injection drug solution M without an intervening delay. Accordingly, the cartridges 7 into which the injection drug solution M is poured must be capable of providing an extremely tight seal so that they can be stored for a reasonably long time.

In the present embodiment, it is possible to secure the interior of the cartridge 7 in a sealed state right up until the freeze-drying step S30, and the inside and outside of the cartridges 7 can be easily allowed to communicate with each other only when the injection drug solution M is to be freeze-dried. Accordingly, it is possible to manufacture dual chamber combined container-syringes that have high levels of sterility and productivity, and that are able to be filled with accurate quantities of freeze-dried pharmaceutical products.

Moreover, by performing the substitution processing S33 after the injection drug solution M has been freeze-dried, it is possible to remove moisture evaporated from the injection drug solution M from the surrounding atmosphere. Accordingly, moisture can be prevented from remaining inside the cartridge 7, and it is possible to maintain a high quality of freeze-dried pharmaceutical product S.

Furthermore, by performing the sealing processing S34 at the end of the freeze-drying step S30, and pushing the front plunger 2 inside the cartridge 7, it is possible to reliably maintain the freeze-dried pharmaceutical product S which is formed by freeze-drying the injection drug solution M in a tightly sealed state.

Moreover, according to the front plunger 2 of the present embodiment, as a result of the first sealing rib 2b and the second sealing rib 2c tightly adhering to the inner circumferential surface of the cartridge 7 when they have been inserted inside it, it is possible to secure air-tightness and fluid-tightness in the cartridge 7. Moreover, when the front plunger 2 has been moved as far as the distal end of the cartridge 7 by the difference in pressures between the inside and outside of the cartridge 7 and is placed in the cartridge 7 in the exchange state, the inside and outside of the cartridge 7 are able to communicate with each other by means of the communicating grooves 2i. As a result of this, freeze-drying can be reliably performed on the injection drug solution M inside the cartridges 7.

Moreover, in this exchange state of the front plunger 2, even if the first sealing rib 2b and the second sealing rib 2c escape to the outside of the cartridge 7, because the positioning rib 2a is still trapped inside the cartridge 7, the front plunger 2 is prevented from accidentally coming out of the cartridge 7. Accordingly, the sealing processing S34 in the freeze-drying step S30 can be reliably performed.

Furthermore, because the first sealing rib 2b is provided with the inclined surface 2h, even if the inside and outside of the cartridge 7 are able to communicate with each other by means of the communicating grooves 2i before the first sealing rib 2b has completely escaped from the cartridge 7, the escape of the first sealing rib 2b from the cartridge 7 is accelerated by the elasticity of the first sealing rib 2b and by the inclined surface 2h. Because the first sealing rib 2b sits at the distal end of the cartridge 7 as a result of escaping from the interior of the cartridge 7 in this manner, it is possible to improve the stability of the front plunger 2 which is located in the cartridge 7 in the exchange state.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

LIST OF REFERENCE NUMERALS 2 front plunger
2a positioning rib
2b first sealing rib
2c second sealing rib
2d inner end side
2e outer end side
2f first valley portion
2g second valley portion
2h inclined surface
2i communicating groove
3 opening end
4 opening edge
5 longitudinal portion
6 combined container-syringe
7 cartridge
7a bypass portion
8 front assembly
9 finger grips
10 middle plunger
11 end plunger
A internal air
L diluent
M drug solution
O center axis
P pressure
R1 clean room
R2 freeze-drying chamber
S freeze-dried pharmaceutical product

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Materials:
  100 Glass carpules with inner micro bypass, washed and baked-in siliconized
  100 End stoppers—cleaned and manually siliconized
  100 Lyo-stoppers (front stoppers) (cavity H)
  50 middle stoppers with no ribs (type 1)—cleaned and manually siliconized
  50 middle stoppers with 3 ribs (type 2)—cleaned and manually siliconized
  Diluent WFI, freshly degased
  Placebo solution trehalose 5%

A) Bubble Free Filling and Autoclaving of Diluent

Positioning of end stopper using stoppering machine→Filling of 1.0 mL diluent using a high precision pipette→Positioning of middle stopper (50% type 1 and 50% type 2) in the bypass area→placing distance rods into carpules→transferring of carpules in the freeze dryer and cooling down to 5° C.→drawing of vacuum to 12 mbar→depressing the middle stopper down into final position→venting of the freeze dryer and unloading→loading of the autoclave and autoclaving (121° C. for 20 min)→drying of the carpules at 80° C. for 8 hours (to reduce humidity of middle stopper) (see FIGS. 9A to 9H.

Result and Conclusion:

Any air bubble that was present was removed when vacuum was applied in the freeze dryer. The air is sucked out of the grooves of the end stopper into the diluent due to the small ribbs of this stopper. The air is vented via the bypass channels.

The process of positioning the middle stopper in the freeze dryer under vacuum for bubble free filling of is very easy and works smoothly. The carpules are virtually bubble-free after filling and only a small air bubble is visible after autoclaving (Most likely residual air is pressed out of the grooves of the end stopper into the diluent). The applicants tested both types of middle stoppers, type 1 (with no ribs) and type 2 (with 3 ribs) and both turned out to be suitable (see FIG. 9I).

B) Filling of Lyo-Solution and Opening of Lyo-Stoppers in the Freeze Dryer by Vacuum Filling of 1.0 mL placebo solution using a high precision pipette→positioning of thermo couples in 4 carpules→positioning of lyo stopper using B+S stoppering machine→loading of the carpules (100) into the freeze dryer→freezing at −45° C. for 5 hours→opening of the lyo channels by lifting the lyo stoppers under vacuum (see FIG. 10A to 10D).

Result and Conclusion:

The lyo stoppers of all carpules were lifted into the desired position without any failure. This critical process can be regarded as safe and reproducible.

C) Freeze-Drying and Closing of the Lyo Chamber

Figure 11:
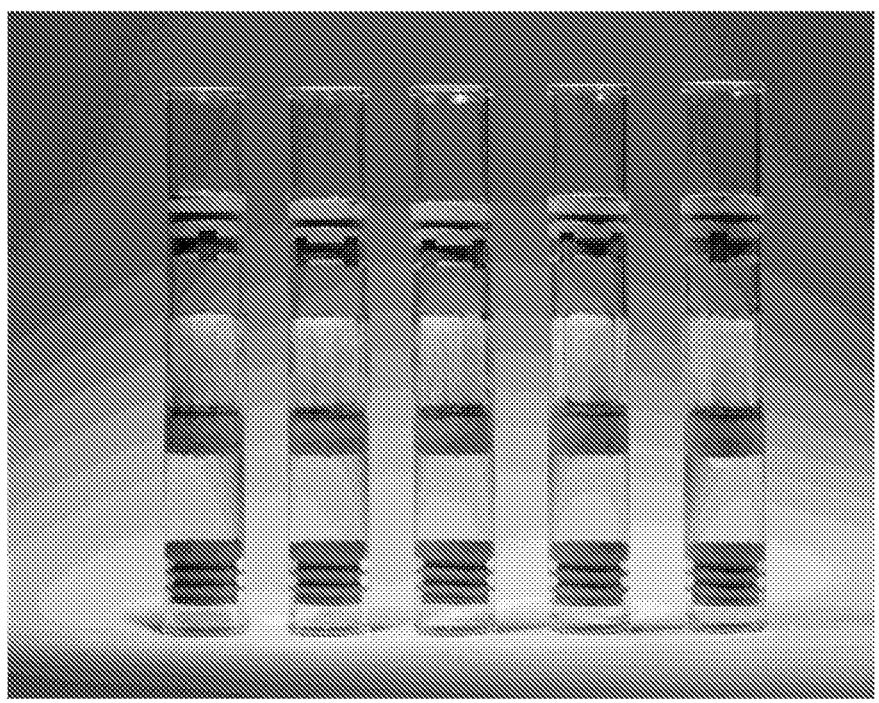
FIG. 11 shows filled Lyo-DCPS with middle stoppers (plungers) without ribs

The placebo solution was lyophilized by means of a prototype lyo cycle of approx. 60 hours duration. Lyo-stopper were depressed back into the carpules by collapsing the lyo shelves together at a defined vacuum. The chamber was vented afterwards to further suck the lyo stopper into its final position (see FIG. 11).

Result and Conclusion:

1 mL trehalose solution was turned into a perfect lyo-cake without any collapse or meltback. All lyo cakes look identical.

The invention claimed is:

1. A device for sealing a vessel, in particular a cartridge or a test-tube for accommodating a freeze-dried pharmaceutical product, wherein the vessel comprises at its opening end an opening edge and an adjoining longitudinal portion with an evenly formed inner cross section, the device comprising:
   a front plunger to be positioned inside the vessel at the longitudinal portion,
   wherein the front plunger is configured to be positioned in the vessel in a sealing state, in which the front plunger is fully inserted in the vessel, or in an exchange state, in which the front plunger is inserted partly in the vessel and partly protrudes over the opening edge of the vessel, so that when a pressure difference is provided between the inside and the outside of the vessel, the front plunger is capable of moving from the sealing state towards the opening end of the vessel until it is positioned in the exchange state and further comprises
      sealing means configured to seal the inside of the vessel against the outside when the front plunger is positioned in the sealing state, and
      one or more communicating grooves configured to place the inside and outside of the vessel in communication with each other when the front plunger is positioned in the exchange state,
      wherein the one or more communicating grooves are formed in an outer circumferential surface of the front plunger and extend from an inner end side of the front plunger into a first sealing rib of the front plunger.

2. The device according to claim 1, wherein the outer form of the first sealing rib is adapted to the form of the inner cross section of the longitudinal portion.

3. The device according to claim 2, wherein the inner cross section of the longitudinal portion has a circular form, and wherein the first sealing rib has an outer diameter that is larger than the inner diameter of the longitudinal portion, and that is configured to elastically contract when the front plunger is positioned inside the vessel so as to form a tight seal with the inner surface of the longitudinal portion.

4. The device according to claim 2, wherein the first sealing rib is dimensioned in such a way that the front plunger, when an underpressure of predefined strength is applied to the outer environment of the vessel, is caused to move inside the vessel toward the opening end of the vessel.

5. The device according to claim 2, wherein an inclined surface extending in a circumferential direction of the first sealing rib is formed at a rear end portion of the first sealing rib, wherein the diameter of the inclined surface gradually expands as it moves from the rear end side toward the front end side.

6. The device according to claim 2, wherein the one or more communicating grooves extend from the inner end side of the front plunger up to the center of the first sealing rib in the direction of a center axis of the front plunger.

7. The device according to claim 2, wherein the sealing means includes a positioning rib whose outer diameter is substantially the same as the inner diameter of the longitudinal portion of the vessel, the positioning rib being positioned further to the inner end side of the front plunger than the first sealing rib, so as to remain inside the vessel when the front plunger is positioned in the exchange state.

8. The device according to claim 1, wherein the communicating grooves are formed at intervals in the circumferential direction of the front plunger.

9. A dual chamber combined container-syringe, comprising;
   the device according to claim 1;
   a cartridge, in which the front plunger, a middle plunger, and an end plunger are positioned in this sequence from the opening end,
   a diluent, which is sealed inside the cartridge between the end plunger and the middle plunger, and
   a freeze-dried pharmaceutical product, which is sealed inside the cartridge between the middle plunger and the front plunger.

10. A front stopper comprising:
   a sealing rib whose outer diameter is larger than an inner diameter of a cartridge, the sealing rib configured to elastically contract when the sealing rib is inserted inside the cartridge so as to form a tight seal with an inner circumferential surface of the cartridge;
   a positioning rib that is positioned further to a rear end side than the sealing rib and whose outer diameter is substantially the same as the inner diameter of the cartridge; and a
   communicating groove that is formed in an outer circumferential surface of the front stopper, the communicating groove extending from the positioning rib into the sealing rib and being configured to place the inside and outside of the cartridge in communication with each other when the front stopper is placed in the cartridge in a half stoppering state.

\* \* \* \* \*